(12) United States Patent  
Chu

(10) Patent No.: US 8,409,243 B2
(45) Date of Patent: Apr. 2, 2013

(54) ENDOSCOPIC APPARATUS AND METHOD

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 776 days.

(21) Appl. No.: 11/640,251

(22) Filed: Dec. 18, 2006

(65) Prior Publication Data

US 2007/0167677 A1 Jul. 19, 2007

Related U.S. Application Data

(62) Division of application No. 10/000,325, filed on Dec. 4, 2001, now Pat. No. 7,169,167.

(51) Int. Cl.
*A61B 17/00* (2006.01)
(52) U.S. Cl. ...................................................... 606/205
(58) Field of Classification Search ................ 600/104, 600/106; 606/170, 174, 205, 206, 208
See application file for complete search history.

(56) References Cited

U.S. PATENT DOCUMENTS

| 3,958,576 | A |   | 5/1976  | Komiya |
| 4,590,936 | A | * | 5/1986  | Straub et al. ............... 606/174 |
| 4,712,547 | A | * | 12/1987 | Bonnet ....................... 606/170 |
| 4,763,668 | A | * | 8/1988  | Macek et al. ............... 600/564 |
| 5,275,612 | A |   | 1/1994  | Bales, Jr. |
| 5,318,589 | A |   | 6/1994  | Lichtman |
| 5,471,992 | A |   | 12/1995 | Banik et al. |
| 5,496,347 | A |   | 3/1996  | Hashiguchi et al. |
| 5,584,855 | A | * | 12/1996 | Onik ........................... 606/207 |
| 5,603,711 | A | * | 2/1997  | Parins et al. ................. 606/51 |
| 5,603,723 | A | * | 2/1997  | Aranyi et al. ............... 606/205 |
| 5,636,639 | A | * | 6/1997  | Turturro et al. ............ 600/564 |
| 5,697,940 | A |   | 12/1997 | Chu et al. |
| 5,728,117 | A |   | 3/1998  | Lash |
| 5,755,732 | A | * | 5/1998  | Green et al. ................ 606/170 |
| 5,843,000 | A | * | 12/1998 | Nishioka et al. ............ 600/566 |
| 5,846,248 | A |   | 12/1998 | Chu et al. |
| 5,849,022 | A |   | 12/1998 | Sakashita et al. |
| 5,961,526 | A |   | 10/1999 | Chu et al. |
| 6,051,003 | A |   | 4/2000  | Chu et al. |
| 6,053,877 | A | * | 4/2000  | Banik et al. ................. 600/566 |
| 6,059,719 | A |   | 5/2000  | Yamamoto et al. |

(Continued)

FOREIGN PATENT DOCUMENTS

EP 316816 A1 * 5/1989
JP H06-343599 A 12/1994

*Primary Examiner* — Ryan Severson
*Assistant Examiner* — David Eastwood
(74) *Attorney, Agent, or Firm* — Bookoff McAndrews, PLLC

(57) ABSTRACT

The present invention is directed to a medical device, such as an endoscopic device, configured to be loaded into a channel of an endoscope prior to insertion of the endoscope into a body, and a method of performing an operative procedure with an endoscopic device. The endoscopic device comprises an elongate member for insertion into the channel of the endoscope, wherein a length of the elongate member is greater than a length of the channel of the endoscope. The endoscopic device also comprises a distal assembly connected to a distal portion of the elongate member and operable to perform an endoscopic operation, wherein the distal assembly has an open configuration and a closed configuration with a profile larger than a diameter of the channel of the endoscope, wherein the distal assembly is adapted to be exterior to the channel when the endoscope is inserted into the body.

24 Claims, 17 Drawing Sheets

U.S. PATENT DOCUMENTS

| | | | |
|---|---|---|---|
| 6,066,102 A * | 5/2000 | Townsend et al. | 600/564 |
| 6,142,956 A | 11/2000 | Kortenbach et al. | |
| 6,193,737 B1 | 2/2001 | Ouchi | |
| 6,206,904 B1 | 3/2001 | Ouchi | |
| 6,210,416 B1 | 4/2001 | Chu et al. | |
| 6,235,040 B1 | 5/2001 | Chu et al. | |

* cited by examiner

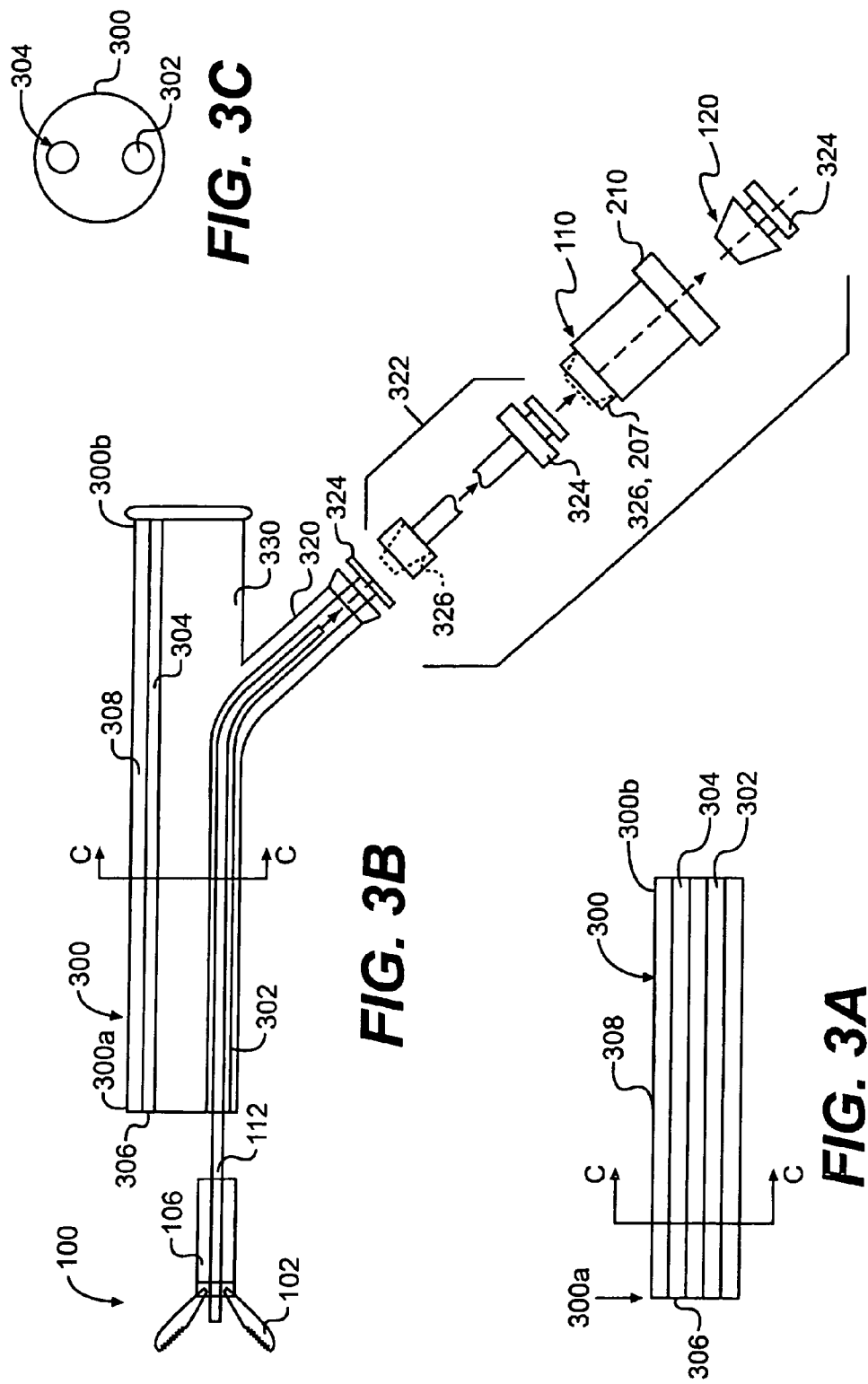

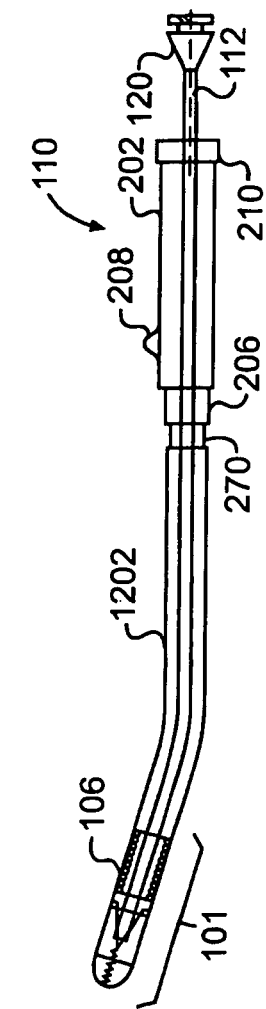
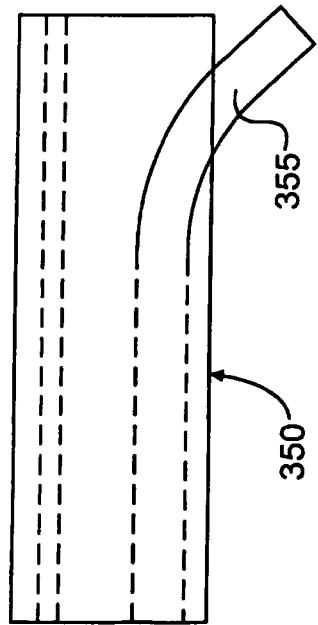
FIG. 12A
FIG. 12B

ENDOSCOPIC APPARATUS AND METHOD

CROSS-REFERENCE TO RELATED APPLICATIONS

This is a divisional application of U.S. patent application Ser. No. 10/000,325, filed Dec. 4, 2001 now U.S. Pat. No. 7,169,167, the entirety of which is incorporated herein by reference.

DESCRIPTION OF THE INVENTION

1. Field of the Invention

The present invention relates generally to endoscopic devices, including those used for obtaining biopsies or for performing other medical procedures. More particularly, the present invention relates to an endoscopic device having a suitably large distal assembly to properly perform its intended function.

2. Background of the Invention

Endoscopic devices for use in medical procedures typically are passed through a working channel of an endoscope positioned in a body cavity in order to reach an operative site at a distal end of the endoscope. For purposes of this description, "distal" refers to the end extending into a body and "proximal" refers to the end extending out of the body. The size of a distal assembly on the distal end of the endoscopic device, such as a forceps, stent delivery devices, biopsy needles, and electrocoagulation probes, is limited by the diameter of the endoscope's working channel. Because the endoscopic device, such as ureterscope, is passed through a body cavity, such as a urethra, esophagus, or ureter, the diameter of the endoscope, the working channel, and therefore the distal assembly on the endoscopic device threaded through the working channel, are often necessarily small.

For example, an endoscopic device may include a distal assembly, such as forceps, that typically consists of two jaw-like members located distally on an end of a long, flexible tube or sheath. Each jaw member has teeth, a sharp edge, or a similar gripping and cutting mechanism. The jaw members are operable to open and close, enabling the jaws to grasp and cut away tissue for biopsy sampling. The jaw members must be small enough to fit through the working channel of the endoscope, however, which limits the size of the tissue samples obtained. A 3 french ("Fr.") forceps device that fits in a 7 Fr. ureterscope acquires tissue samples that are often too small to be accurately evaluated. The size limitation of the jaws also prohibits the use of forceps for other applications, such as grasping gall stones and kidney stones or removing or displacing larger size tissue samples. A working channel of an endoscope that is sized to accommodate a larger diameter endoscopic device can inhibit both the flexibility of the endoscope and/or the ability of the endoscope to house other functional components, such as visualization means, or may increase the outer diameter of the endoscope to an unusable size.

SUMMARY OF THE INVENTION

Accordingly, the present invention is directed to an endoscopic device having a suitably large distal assembly to properly perform its intended function and configured to be loaded into a working channel of an endoscope, and a method of performing an operative procedure with the endoscopic device.

One aspect of the present invention is directed to an endoscopic device configured to be loaded into a channel of an endoscope prior to insertion of the endoscope into a body. The endoscopic device comprises an elongate member for insertion into the channel of the endoscope, wherein a length of the elongate member is greater than a length of the channel of the endoscope. The endoscopic device also comprises a distal forceps assembly connected to a distal portion of the elongate member and operable to perform an endoscopic operation, wherein the distal forceps assembly has a closed configuration with a diameter larger than a diameter of the channel of the endoscope, wherein the distal forceps assembly is adapted to be exterior to the channel when the endoscope is inserted into the body.

According to another aspect, the present invention is directed to a medical device, comprising an endoscope with a channel having a length; an elongate member for insertion into the channel, and having a length greater than the length of the channel; and a distal forceps assembly connected to a distal portion of the elongate member and operable to perform an endoscopic operation. The distal forceps assembly has a closed configuration with a diameter larger than a diameter of the channel of the endoscope, wherein the distal forceps assembly is adapted to be exterior to the channel when the endoscope is inserted into the body.

According to another aspect, the present invention is directed to a method of performing an operative procedure with an endoscopic device having a distal forceps assembly, comprising loading the endoscopic device into a channel of an endoscope, inserting the endoscope and the endoscopic device into a body while the distal forceps assembly is exterior the channel, positioning the distal forceps assembly proximate an operative site, and activating the distal forceps assembly to perform the operative procedure.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate the various features and aspects of the endoscopic device and its use in an endoscopic procedure, and together with the description, serve to explain its advantages and principles. Notably, the drawings are not to scale, as the endoscope should be long enough to traverse long passageways in the body to an operative site.

FIGS. 3a through 3c are exemplary endoscopes for use in connection with an endoscopic device, consistent with embodiments of the present invention. FIG. 3a is a cross-sectional of an endoscope. FIG. 3b is a plan view of another endoscope with a sidearm, shown in combination with an endoscopic device according to an embodiment of the present invention. FIG. 3c is a cross sectional view of the exemplary endoscopes in FIGS. 3a and 3b taken along lines c-c in FIGS. 3a and 3b.

In FIG. 8a, the distal forceps assembly of the endoscopic device is open to its normal open position. In FIG. 8b, the distal forceps assembly of the endoscopic device is opened beyond its normal open position.

FIG. 10a is the endoscopic device. FIG. 10b is the endoscopic device in FIG. 10a in a closed position and loaded in an endoscope. FIG. 10c is the endoscopic device in FIG. 10a in an open position and loaded in an endoscope.

FIGS. 12a-12b are a plan view of another exemplary endoscopic device that is back-loaded into an endoscope with a large working channel. The exemplary endoscopic device is illustrated in FIG. 12a, and an exemplary endoscope is illustrated in FIG. 12b.

DETAILED DESCRIPTION

Reference will now be made in detail to implementations of the endoscopic devices and methods of use as illustrated in the accompanying drawings. Wherever possible, the same reference numbers will be used throughout the drawings to refer to the same or like parts.

FIGS. 1-12 illustrate exemplary embodiments of endoscopic devices and methods of their use consistent with the present invention. An advantage of the present invention, as illustrated in the embodiments shown in the accompanying drawings, is that the device's distal forceps assembly that performs an operative procedure, such as obtaining biopsies or removing stones, is sufficiently large in size to perform the operative procedure. For example, because the size of the distal assembly of the endoscopic device can be larger than the diameter of a working channel of the endoscope into which the endoscopic device is loaded, larger biopsy samples can be obtained, or larger stones can be removed or held. At the same time, additional instruments, such as laser probes, lithotripters, and devices to perform suction, irrigation, injection, severance, or guidance, may be inserted through a shaft of the endoscopic device to enhance the procedure or to perform additional operative procedures.

Figure 1A:
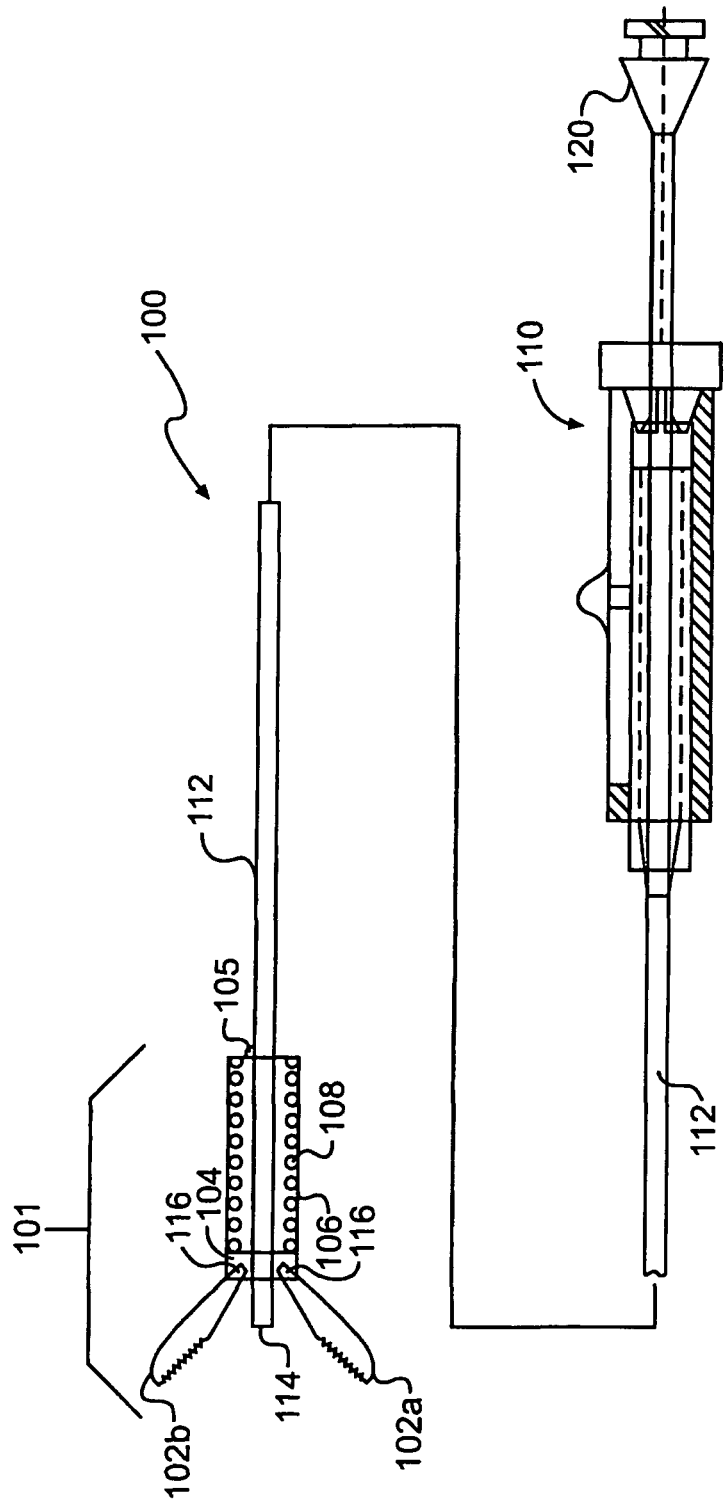
FIG. 1a is a plan view of an exemplary endoscopic device with a proximal handle.

FIG. 1a illustrates an endoscopic device 100 according to an embodiment of the present invention. Endoscopic device 100 includes a distal forceps assembly 101 connected to a proximal handle 110 and a hub 120 by an elongate member, such as a shaft 112. An exemplary distal forceps assembly 101, the components of which are illustrated in an exploded view in FIG. 1b, has a pair of jaw members 102a,b mounted on a ring 104 housed internally within a tube 106. Tube 106 also may house a spring 108, which abuts ring 104. Tube 106, ring 104, and spring 108 surround the elongate member, such as shaft 112. Shaft 112 may include a lumen 114 and a stop 105. Shaft 112 is attached distally to ring 104 and may also pass through proximal handle 110 and attach proximally to hub 120. Endoscopic device 100 is in an open position in FIGS. 1a and 1b, which is the "normal" position requiring no activation by an operator. Jaw members 102a,b are activated to close and reopen by proximal handle 110, the operation of which will be described.

Lower jaw member 102a and upper jaw member 102b pivotally attach to ring 104 and are operable to open and close. Although jaw members 102a,b illustrated in FIG. 1 have teeth for sampling tissue and performing other operative procedures, jaw members 102a,b may alternatively have a sharp edge or some other suitable characteristic for performing operative procedures.

Figure 1B:
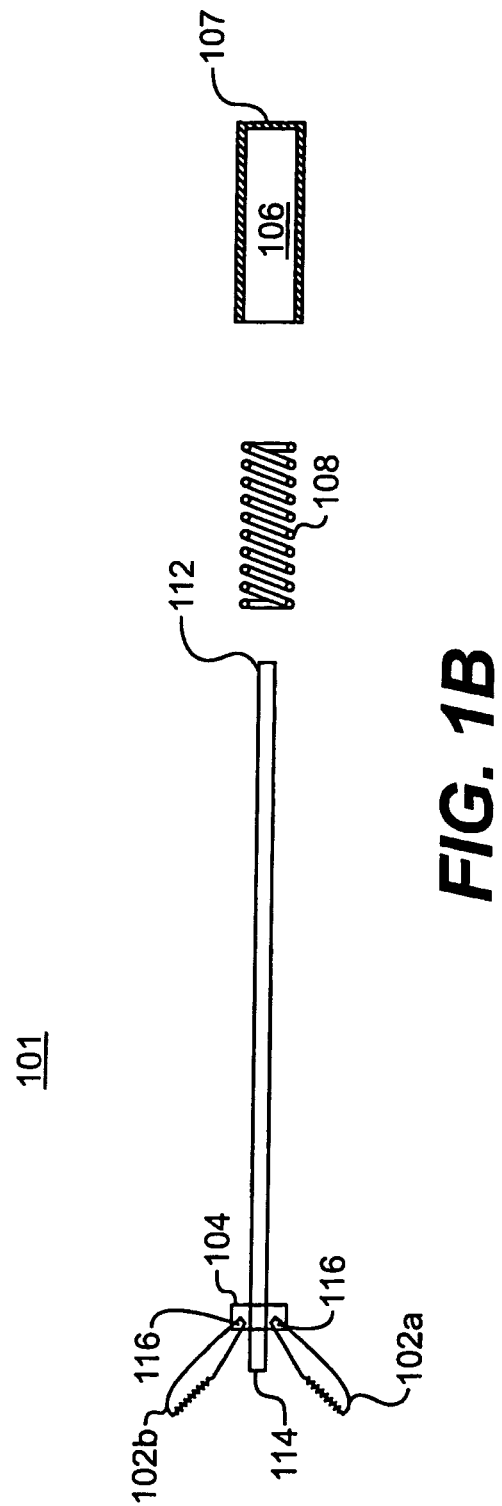
FIG. 1b is an exploded view of the distal forceps assembly illustrated in FIG. 1a, consistent with an embodiment of the present invention.

When jaw members 102a,b are open, as in FIGS. 1a and 1b, lower jaw member 102a is separated from upper jaw member 102b in a "normal" position. The normal, open position is dictated, at least in part, by an appropriate attachment mechanism and/or method at attachment locations 116 of lower jaw member 102a and upper jaw member 102b to ring 104. An appropriate mechanism might include a pivot pin or screw, and appropriate methods might include welding or swagging, or any other suitable device or method known in the art to mount jaw members 102a,b pivotally on ring 104 at a distal most end of tube 106, permitting jaw members 102a,b to open in a wide position.

The normal, open position of jaw members 102a,b is further dictated by other characteristics of jaw members 102a,b and remaining parts of distal assembly 101, such as the tightness of the mount of the jaw members to ring 104 and the characteristics of spring 108. Jaw members 102a,b also may be comprised of a biocompatible material having "memory," such as nitinol, which is an elastic shape memory alloy that readily returns to its original shape. Because of these characteristics of jaw members 102a,b and their mount, jaw members 102a,b return to the open position when released from the walls of tube 106 (as will be illustrated and explained with respect to FIGS. 5a and 5b).

When jaw members 102a,b are closed (shown in FIG. 5b), lower jaw member 102a mates with upper jaw member 102b and jaw members 102a,b retract partially into tube 106 along with ring 104. The diameter of closed jaw members 102a,b (designated "d" in FIG. 5b) is smaller than the diameter of tube 106, so that jaw members 102a,b fit within tube 106. At the same time, the diameter of tube 106 is larger that the diameter of a working channel 302 of an endoscope 300 (FIG. 3a-3c).

Ring 104 serves as a mount for an operative component such as jaw members 102a,b, and may be made of any biocompatible material, such as plastic, rubber, or metal, that can accommodate a mounting member, such as a screw. Jaw members 102a,b are attached to ring 104 at attachment locations 116 with mounting members such as screws, pins, or similar mounting devices, as discussed above.

Shaft 112 is elongate and typically flexible or semi-flexible. The length of shaft 112 is longer than the length of the endoscope and the diameter is smaller than the working channel of the endoscope in which it is loaded, as will be discussed in more detail. Shaft 112 passes though and attaches to ring 104, by any suitable means known in the art. A distal portion of shaft 112 extends beyond the distal end of tube 106 and is operable to open jaw members 102a,b when moved manually or in conjunction with proximal handle 110, the operation of which will be discussed.

Tube 106 surrounds shaft 112 and ring 104 having attached jaw members 102, and contains spring 108 in communication with ring 104. The distal end of tube 106 is open, while the proximal end is closed except for a hole 107 through which shaft 112 passes. The proximal end of tube 106 abuts stop 105. Stop 105, such as a welded or rubber stop, is placed or formed on shaft 112 either before or after distal assembly 101 is assembled on a shaft 112. The diameter of hole 107 should be greater than that of shaft 112 but small enough to abut or "catch" stop 105 on shaft 112 to prevent shaft 112 and/or ring 104 from sliding out of the distal end of tube 106. Tube 106 may be comprised of plastic or metal, such as a hypodermic tube, or another fairly rigid, biocompatible material. The internal diameter of tube 106 is greater than the outer diameter of ring 104 having attached jaw members 102. The diameter of spring 108 also is smaller than the internal diameter of tube 106. Spring 108 is compressed in tube 106 when jaws 102a,b are closed (see FIG. 5a) and substantially relaxed in tube 106 when jaws 102a,b are open (FIGS. 1 and 5b). The length of spring 108 when relaxed therefore is the length of tube 106 less the width of ring 104. Although components of distal assembly 101, such as ring 104, tube 106, and spring 108, are round, they may be of any shape (square, rectangular, elliptical, etc.) consistent with the present invention.

Figure 2A:
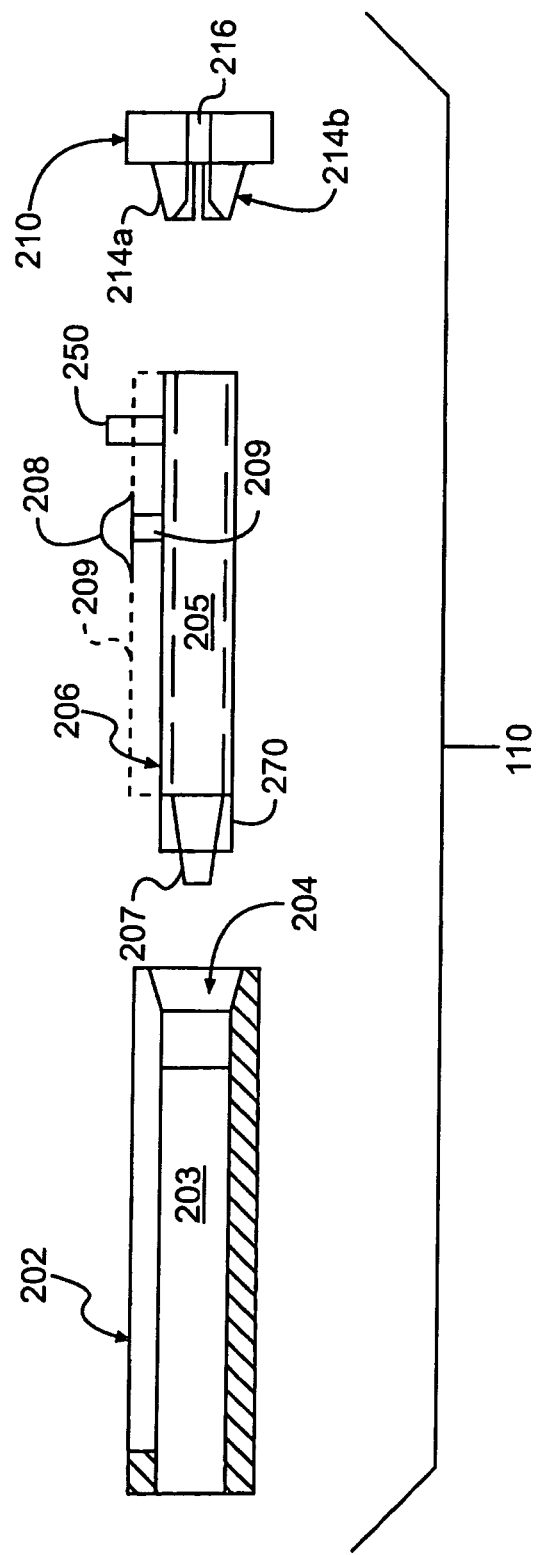
FIGS. 2a and 2b are exploded side and top views, respectively, of the removable proximal handle illustrated in FIG. 1, and FIGS. 2c-2e are exploded, cross-sectional, and plan views, respectively, of another exemplary removable proximal handle, consistent with an embodiment of the present invention.
Figure 2B:
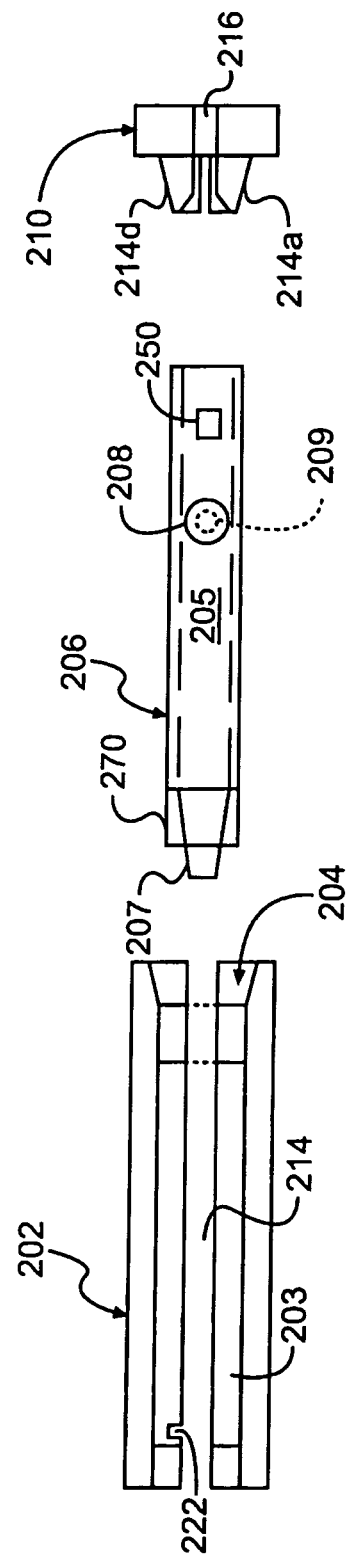

FIGS. 2a and 2b illustrate exploded plan and top views, respectively, of the components of an exemplary removable proximal handle 110 shown in FIG. 1a. Proximal handle is comprised of a casing 202, a slide 206, and a cap 210.

Casing 202 has a cavity 203 for receiving slide 206 and a groove 214 for receiving a connector 209 of a knob 208. The diameter of cavity 203 is greater than the diameter of slide 206. Casing 202 is open at the distal end to allow slide 206 to be partially projected out of casing 202 and drawn back into cavity 203 by moving knob 208 along groove 214. A compression taper 204 is located at a proximal end of casing 202 for receiving compression teeth 214a-214d (214c not shown) of cap 210.

Cap 210 is secured to a proximal end of casing 202. A proximal end of shaft 112 fits into cap 210 and compression teeth 214a-214d compress upon shaft 112, securing shaft 112 to cap 210. Alternatively, cap 210 may have an optional opening 216 for receiving shaft 112, where proximal end of shaft 112 is secured to hub 120 (hub shown in FIG. 1a). In either case, shaft 112 remains fixed with respect to casing 202, although slide 206 is able to be moved relative to casing 202 and shaft 112.

Slide 206 is slideably disposed within cavity 203 of casing 202 and has knob 208 attached to slide 206 by connector 209 that is receivable by groove 214. Connector 209 may extend to knob 208 (solid line) only or may extend along the length of slide 206 (dashed line). Slide 206 also has a tapered lumen 205 within a cover 270 configured to receive shaft 112 of endoscopic device 100. The diameter of a most distal end 207 of tapered lumen 205 is therefore larger than the diameter of shaft 112. Even when slide 206 is fully withdrawn into cavity 203, a portion of slide 206, including cover 270 and distal end of tapered lumen 207, projects out of casing 202.

Cap 210 fitted in casing 202 prevents slide 206 from sliding out the proximal end of casing 202. Casing 202, slide 206, or both, also are configured with a stop mechanism to prevent slide 206 from sliding out the distal end of casing 202. For example, groove 214 may extend through the distal end of casing 202 and have a lock slot 222 on its distal end and located on one side of groove 214 for locking slide 206 by positioning connector 209 of knob 208 in lock slot 222. Lock slot 222 prevents slide 206 from moving in a proximal direction, essentially keeping jaw members 102a,b closed, as will be described.

Figure 2C:
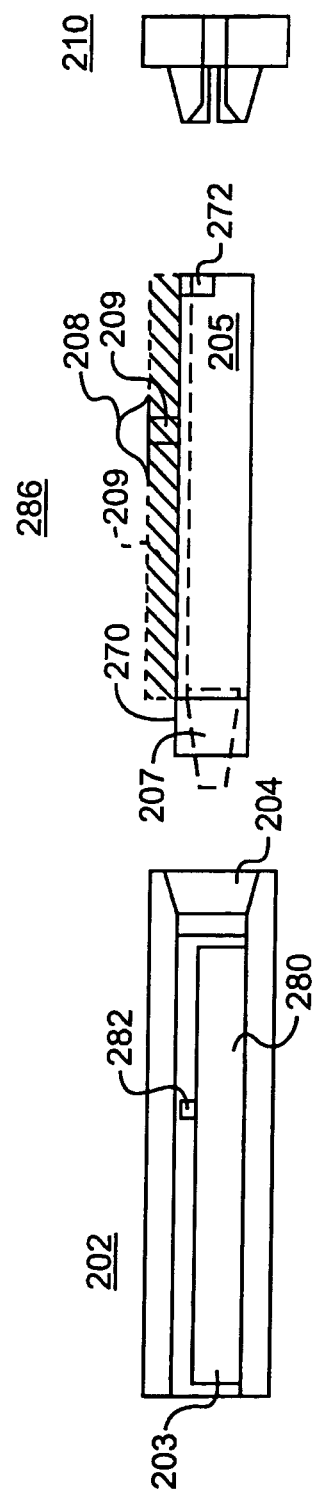
Figure 2D:
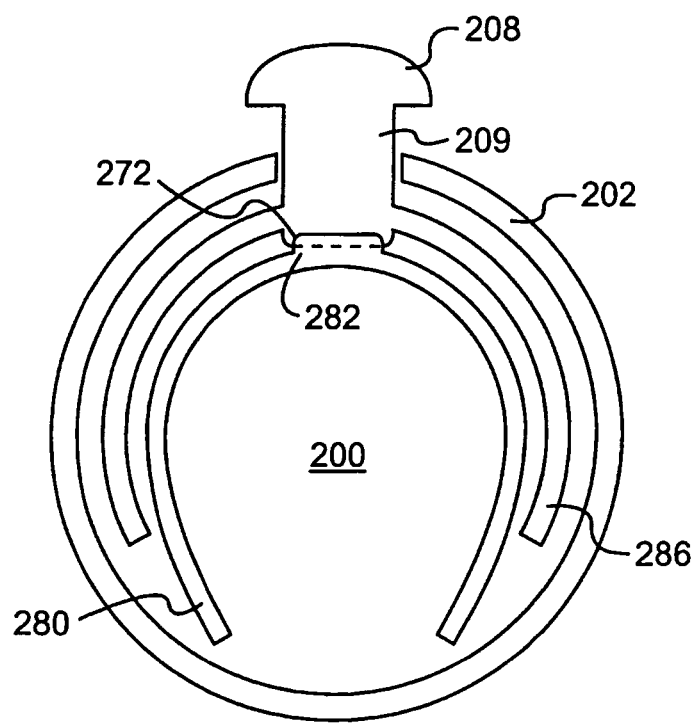
Figure 2E:
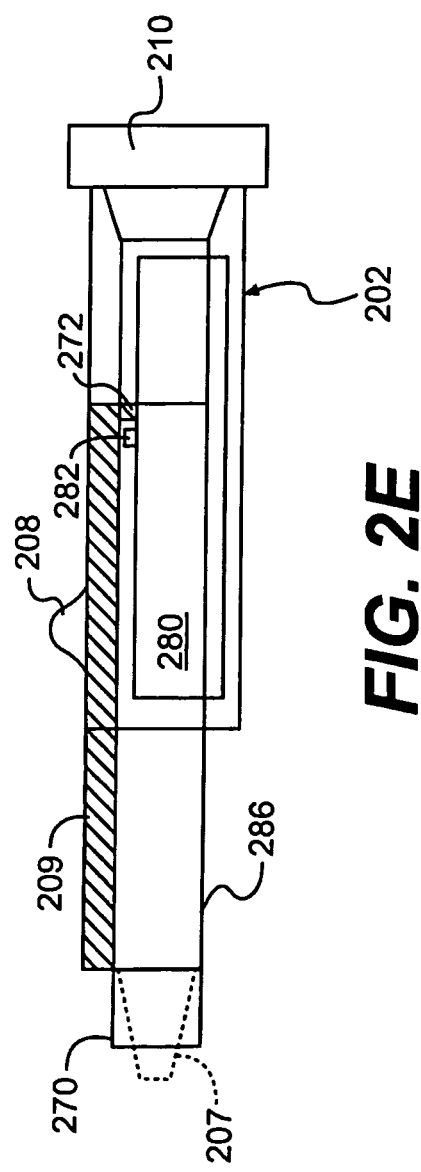

An alternative embodiment of proximal handle 110 is illustrated with respect to FIGS. 2c-2e. Generally, the structure of casing 202 is similar to that of FIGS. 2a and 2b, except that casing 202 includes a support 280 with a projection 282. Support 280 is a semicircular ring that fits within casing 202, as shown in FIG. 2d. Support 280 supports a slide 286 having a projection 272. Slide 206 is also a semicircular ring and is configured to mate with support 280. When slide 206 is extended distally relative to casing 202, its projection 272 eventually comes in contact with support projection 282, which prevents slide 206 from projecting completely out of casing 202, as shown in FIG. 2e. Further alternative constructions of a proximal handle 110 are sufficient for use with endoscopic device 100 illustrated in FIG. 1, provided that the handle is operable to activate distal assembly 101, the activation of which will be discussed.

FIG. 3a is a cross-sectional view of a portion of an exemplary endoscope 300 with a distal end 300a and a proximal end 300b, for use in combination with endoscopic device 100, according to an embodiment of the present invention. Endoscope 300 is a long, flexible tube 308 having a working channel 302 and an optic channel 304 extending the length of endoscope 300, as shown in FIG. 3a and FIG. 3c (cross sectional view along the width of endoscope 300). Optic channel 304 may contain a fiber optic cable with a viewport 306 at distal end 300a, or another viewing device such as a miniature camera, with which an operator may view the operative site from proximal end 300b after endoscope 300 is inserted into a body cavity. Shaft 112 is inserted through working channel 302. Thus, the cross-sectional size of working channel 302 is greater than the cross-sectional size of shaft 112.

FIG. 3b is a plan view of another exemplary endoscope 300 for use in combination with endoscopic device 100, according to an embodiment of the present invention. Endoscope 300 includes a main body 330 and a side arm 320 consistent with the present invention. Shaft 112 passes through working channel 302 of main body 330 and side arm 320, and the proximal end of shaft 112 is connected to cap 210 as previously described. When endoscope 300 is inserted into the body, side arm 320 enables an operator to easily view the operative site with viewport 306 from proximal end 300b of endoscope 300, while an assistant or the operator simultaneously operates distal assembly 101 of endoscopic device 100 via proximal handle 110 from the side. In comparison with endoscope 300 in FIG. 3a, the arrangement shown in FIG. 3b provides the operator, such as a surgeon, with more room to view the operative site.

Optionally, a distal end of an extension 322 may be connected to side arm 320 of endoscope 300, as shown in FIG. 3b. Alternatively, although it is not shown, this extension 322 may also be connected to proximal end of endoscope 300b of the endoscope illustrated in FIGS. 3a and 5a. A proximal end of extension 322 is connected to a distal end of proximal handle 110. To secure the connection, extension 322 may be fitted with a male luer 326 on the distal end and a female luer 324 on the proximal end. Sidearm 320 in FIG. 3b (or alternatively proximal end of endoscope 300b in FIG. 3a) is then formed or fitted with female luer 324, and proximal handle 110 has male luer 326 attached on distal end of taper 207 for connecting to female luer 324 on the appropriate end of extension 322. When extension 322 is used, shaft 112 passes out of side arm 320 (or alternatively endoscope 300), through extension 322, and is secured to cap 210 of proximal handle 110 or to hub 120, as previously described.

Endoscopes 300 illustrated in FIGS. 3a and 3b are examples only, and any suitable endoscope 300 with a working channel 302 may be used in combination with endoscopic devices of the present invention.

FIGS. 4-9 illustrate the operation of endoscopic device 100 of FIG. 1a in conjunction with proximal handle 110 (FIGS. 2a-2c) and endoscope 300 (FIGS. 3a-3c). Generally, the operation includes the following broad steps: (1) endoscope 300 is inserted into the body and guided to an operative site after endoscopic device 100 is loaded into endoscope 300; (2) distal forceps assembly 101 is activated to perform an operation; and (3) endoscope 300 is then removed from the body along with endoscopic device 100.

Figure 4:
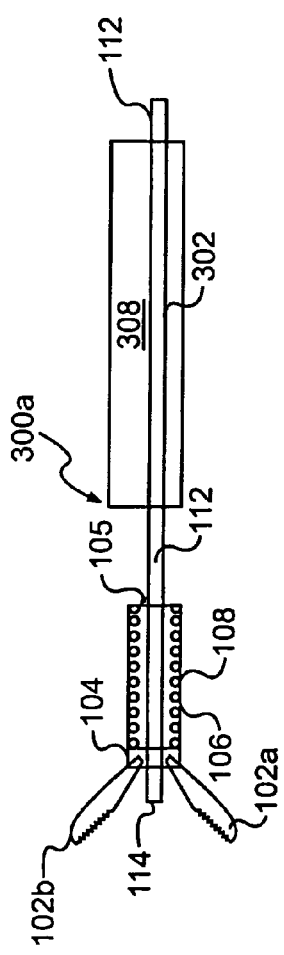
FIG. 4 is a plan view of an exemplary endoscopic device being loaded into an endoscope, consistent with an embodiment of the present invention.

FIG. 4 is a plan view of the endoscopic device of FIG. 1a being loaded into endoscope 300, consistent with an embodiment of the present invention. Proximal handle 110 is removed from shaft 112 by removing cap 210, releasing compression teeth 214a-d, and withdrawing the proximal end of shaft 112 from tapered lumen 205. The proximal end of shaft 112 is then loaded into working channel 302 at distal end 300a of endoscope 300, i.e., endoscopic device 100 is front-loaded into endoscope 300.

Back loading, the more common procedure for advancing an endoscopic device into an endoscope, occurs when an endoscopic medical instrument is loaded into an endoscope at the proximal end after the endoscope has already been inserted into the body cavity to reach the operative site. Front-loading occurs when the medical instrument is loaded into endoscope 300 at distal end 300a before endoscope 300 is inserted into the body cavity. In the illustrated example, jaw members 102a,b of distal forceps assembly 101 are larger than the diameter of working channel 302, and therefore endoscopic device 100 is front-loaded before endoscope 300 is inserted into the body.

Once shaft 112 is threaded through working channel 302, proximal handle 110 is reconnected by placing cap 210 on the proximal end of shaft 112, permitting compression teeth 214a-d to secure shaft 112 relative to cap 210 and casing 202 of proximal handle 110. After endoscopic device 100 is loaded into endoscope 300, knob 208 is moved in a distal direction along groove 214 to a stop mechanism, such as lock slot 222, forcing distal assembly 101 to close and retract into tube 106, as will be described. Exemplary distal forceps assembly 101, including jaw members 102a,b, are exterior to and larger than working channel 302 of endoscope 300.

Endoscope 300 is guided to the operative site using viewport 306 of optic channel 304. With this exemplary endoscopic device 100, tube 106 is larger in diameter than working channel 302 but is smaller in diameter than endoscope 300, enabling an operator to view the operative site through viewport 306 using optic channel 304.

Figure 6:
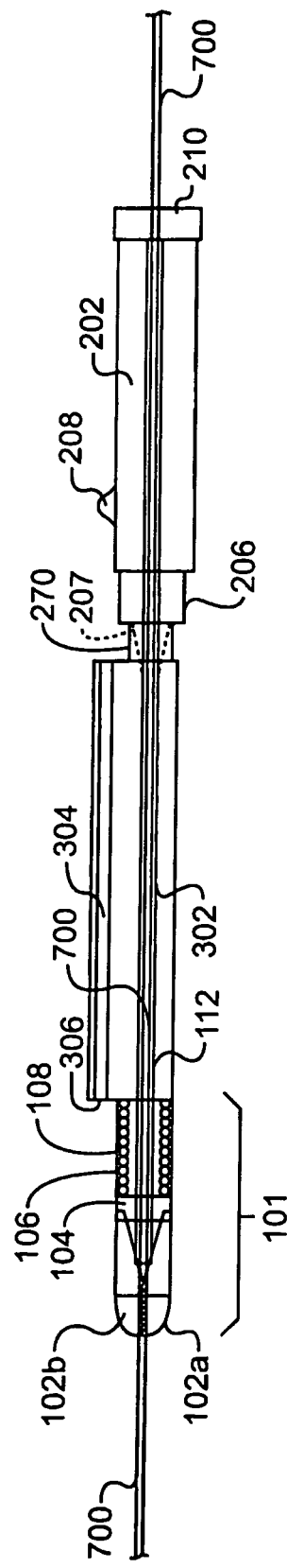
FIG. 6 is a plan view of an exemplary endoscopic device in a closed position that is being introduced with an endoscope to an operative site by a guide, consistent with an embodiment of the present invention.

Optionally, endoscope 300 can be guided to the operative site by a guide 700, shown in FIG. 6. In this example, the operator first inserts guide 700 to the operative site with the aid of an endoscope. The endoscope is removed with guide 700 remaining. After endoscopic device 100 is front-loaded into endoscope 300, the proximal end of guide 700 is inserted into the distal end of shaft 112. At this point, jaw members 102a,b of distal assembly 101 may have already been closed, as described above. Jaw members 102a,b can be opened using proximal handle 110, if necessary, permitting guide 700 to be inserted into jaw members 102a,b and into shaft 112, and then be reclosed so that guide 700 can be threaded between jaw members 102a,b. Endoscope 300 front-loaded with endoscopic device 100 is then guided to the operative site by guide 700 in shaft 112 before distal assembly 101 is activated to gather samples 800 (FIG. 7) or perform another operative procedure. The placement of endoscopic device 100 can be confirmed with fluoroscopy or other suitable imaging procedure. Guide 700 may be a guidewire, or alternatively may be a laser fiber or other mechanism for performing endoscopic procedures.

Figure 5A:
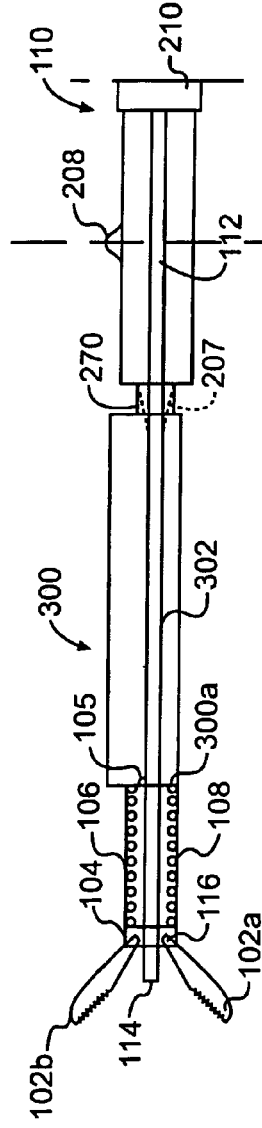
FIGS. 5a and 5b are plan views of the exemplary endoscope and endoscopic device, shown in FIG. 4, in an open and a closed position, respectively, consistent with an embodiment of the present invention.
Figure 5B:
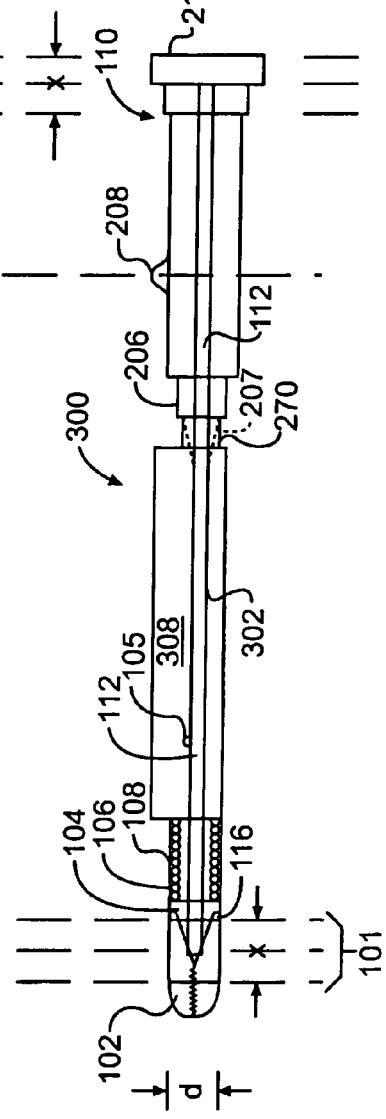

FIGS. 5a and 5b illustrate the activation of exemplary endoscopic device 100 (FIG. 1a) by endoscope 300 (FIGS. 3a-c) in conjunction with proximal handle 110 (FIGS. 2a-c). In FIG. 5a, when jaw members 102a,b are in the normal, open position, tube 106 of distal assembly 101 abuts stop 105 and distal end of endoscope 300a, and proximal end of endoscope 300b abuts the distal end of proximal handle 110. More specifically, proximal end of endoscope 300b abuts cover 270 and distal end 207 of tapered lumen 205 of slide 206. Alternatively, proximal end of endoscope 300b is attached to distal end 207 of tapered lumen 205 by a male luer 324 (e.g., FIG. 3b). Jaw members 102a,b are connected to ring 104, which is connected to shaft 112. The distal end of shaft 112 is held by compression teeth 214 of cap 210 (FIG. 2), forming an operable connection between proximal handle 110 and jaw members 102.

Extension 322 in FIG. 3b can also be used to lengthen the distance from endoscope 300 to proximal handle 110 (not shown), and the same principles of activation described below apply. Using FIG. 5a as a reference, extension 322 would be located between proximal handle and endoscope 300. More specifically, the distal end of extension 322 abuts proximal end of endoscope 300b, and the proximal end of extension 322 abuts cover 270 and distal end 207 of slide 206. To ensure a tighter connection, the distal end of extension 322 may be connected by male or female luer 324, 326 to proximal end of endoscope 300b, and the proximal end of extension 322 is connected by male or female luer 324, 326 to distal end 207 of slide 206.

The operation of proximal handle 110 to activate distal forceps assembly 101, in this instance to close jaw members 102a,b, will now be described with particular reference to FIGS. 2a, 2b, and 5b. When an operator moves knob 208 toward the distal end of proximal handle 110 along groove 214, casing 202 moves proximally a distance x relative to slide 206. Relatively speaking, tapered lumen 207 and slide 206 project a distance x relative to casing 202 of proximal handle 110. As casing 202 moves proximally, shaft 112 moves proximally within slide 206 because shaft 112 is held static with respect to casing 202 by compression teeth 214a-214d of cap 210. Shaft 112 therefore moves proximally a distance x relative to slide 206.

The proximal movement of casing 202 and shaft 112 a distance x relative to slide 206 causes ring 104 to move a distance x proximally relative to proximal handle slide 206 because of the connection between ring 104 and shaft 112 and the previously described abutments of slide 206, endoscope 300, and tube 106. If extension 322 is connected to slide 206 and endoscope 300, the retraction of casing 202 relative to slide 206 similarly causes the shaft of 112 within extension 322 to move proximally a distance x, which in turn causes ring 104 to move proximally relative to tube 106 and proximal handle slide 206.

While shaft 112 (which is interconnected to ring 104 and jaw members 102) moves proximal relative to slide 206, endoscope 300 and tube 106 remain fixed relative to slide 206. As a result, jaw members 102, ring 104, and shaft 112 move a distance x proximally relative to slide 206, while tube 106 remains fixed relative to slide 206, and tube 106 begins to encompass jaw members 102. This proximal movement of shaft 112 and jaw members 102a,b into tube 106 forces jaw members 102a,b to close. Because diameter d of closed jaw members 102a,b, is smaller than the diameter of tube 106, jaw members 102a,b can retract into tube 106. At the same time, spring 108 compresses between ring 104 and the proximal, closed end of tube 106 due to the proximal movement of shaft 112 and ring 104 relative to slide 206 and tube 106. When the operator has pushed knob 208 distally until slide 206 encounters a stopping mechanism (such as the meeting of projections 272 and 282 or projection 250 and lock stop 222), casing 202, shaft 112, and ring 104 have retracted. Because jaw members 102a,b are normally open, and due to the force supplied by spring 108 when jaw members 102a,b are closed, the operator must keep force on knob 208 manually, set connector 209 into lock slot 222, or otherwise ensure casing 202, ring 104, and shaft 112 remain proximal relative to slide 206, spring 108 remains compressed between ring 104 and the proximal end of tube 106, and jaw members 102a,b remain closed.

When the operator removes force from knob 208, for example by releasing pressure or by removing connector 209 from lock slot 222, spring 108 decompresses. The removal of force permits jaw members 102a,b, ring 104, and shaft 112 to move a distance "x" distally, i.e., towards the operative site, relative to proximal handle slide 206. Tube 106 and abutting endoscope 300 remain static relative to proximal slide 206. Jaw members 102a,b therefore release from tube 106 as shaft 112 extends a distance x relative to slide 206 and tube 106, and spring 108 decompresses and assists in releasing jaw members 102a,b from tube 106. Because jaw members 102a,b are normally open as previously described, jaw members 102a,b reopen to the normal position once they are released from tube 106, as shown in FIG. 5a.

Endoscopic device 100 loaded in endoscope 300 with sidearm 320 and extension 322 shown in FIG. 3b operates in substantially the same manner as described for the device in FIGS. 5a and 5b. Briefly, due to the previously described structure, abutments, and connections between components (e.g., FIG. 3b), by moving knob 208 of slide 206 distally, shaft 112, casing 202, and ring 104 move proximally relative to slide 206, scope 300, extension 322, and tube 106 so that normally open jaw members 102a,b close and retract into tube 106.

Figure 7:
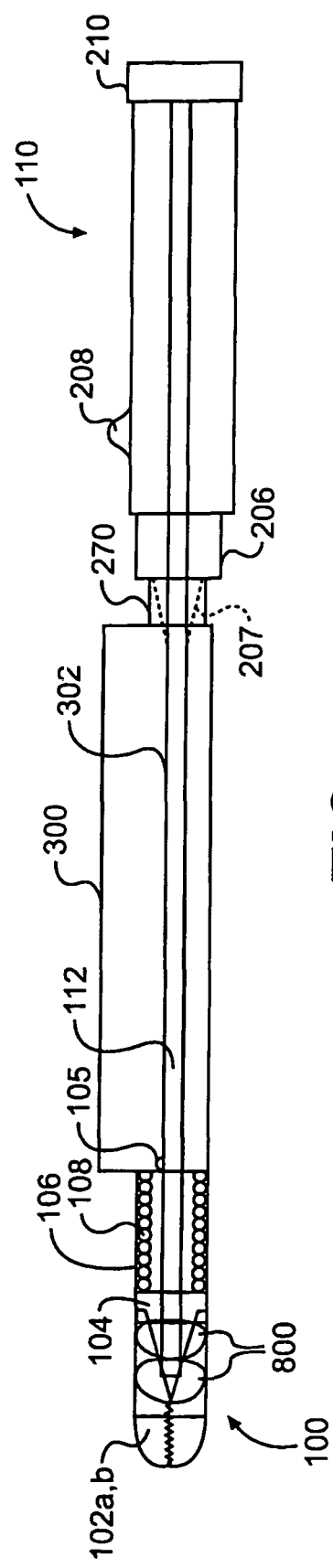
FIG. 7 is a plan view of an exemplary endoscope and endoscopic device in a closed position and storing multiple tissue samples, consistent with an embodiment of the present invention.

One use for endoscopic device 100 is obtaining tissue biopsies. FIG. 7 is a plan view of exemplary endoscopic device 100 in a closed position in endoscope 300 and storing multiple samples 800, consistent with an embodiment of the present invention. Samples 800, such as tissue samples, are stored in closed jaw members 102. Noticeably, due to the size of distal assembly 101, the size of samples 800 that endoscopic device 100 is able to obtain is larger than the diameter of working channel 302, and multiple samples may be obtained and stored. The number of samples 800 that can be stored at one time depends on the size of the samples 800 obtained and the volume within jaw members 102a,b when closed.

Multiple sampling allows multiple biopsy collections in one introduction of endoscope 300 loaded with endoscopic device 100 before samples 800 are removed from the body. When a desired number of samples are gathered, distal assembly 101 is activated to close, and endoscope 300 loaded with endoscopic device 100 is withdrawn from the body. Once out of the body, endoscopic device 100 is activated to open and samples 800 are released from endoscopic device 100. Alternative distal assemblies 101 operate in a similar manner, wherein operative procedures are performed by activation before endoscopic device 100 and endoscope 300 are removed from the body.

Figure 8A:
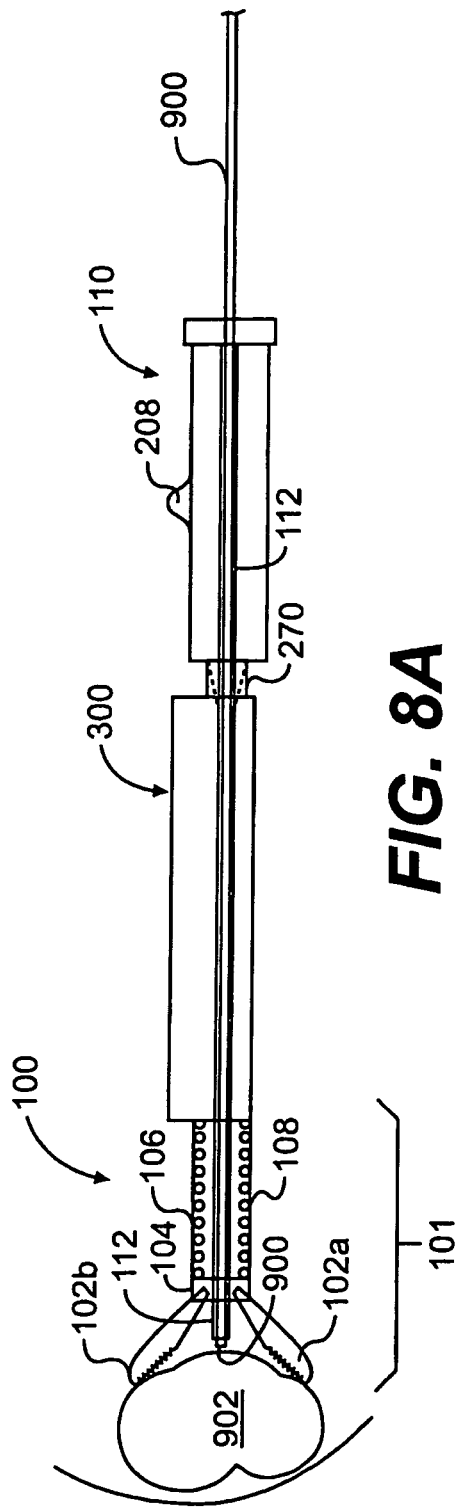
FIGS. 8a and 8b are plan views of an exemplary endoscope and endoscopic device in an open position with a lithotripter for breaking up a stone into small pieces, consistent with an embodiment of the present invention.

Additional operative procedures, such as lithotripsy and injections, may be performed with distal assembly 101 in conjunction with other medical instruments. FIG. 8a is a plan view of an endoscopic device 100 in an open position with a lithotripter 900 for breaking up a stone 902 into small pieces, consistent with an embodiment of the present invention. The stone may be a kidney stone, gallstone, or other undesirable stone. Endoscopic device 100 is open to its normal, open position, and lithotripter 900 extends through shaft 112, exiting shaft 112 distally and proximate to stone 902. Once stone 902 is broken up by lithotripter 900, lithotripter 900 may be proximally withdrawn from shaft 112 and endoscopic device 100 may be used to gather pieces of stone 902 that were broken off.

Figure 8B:
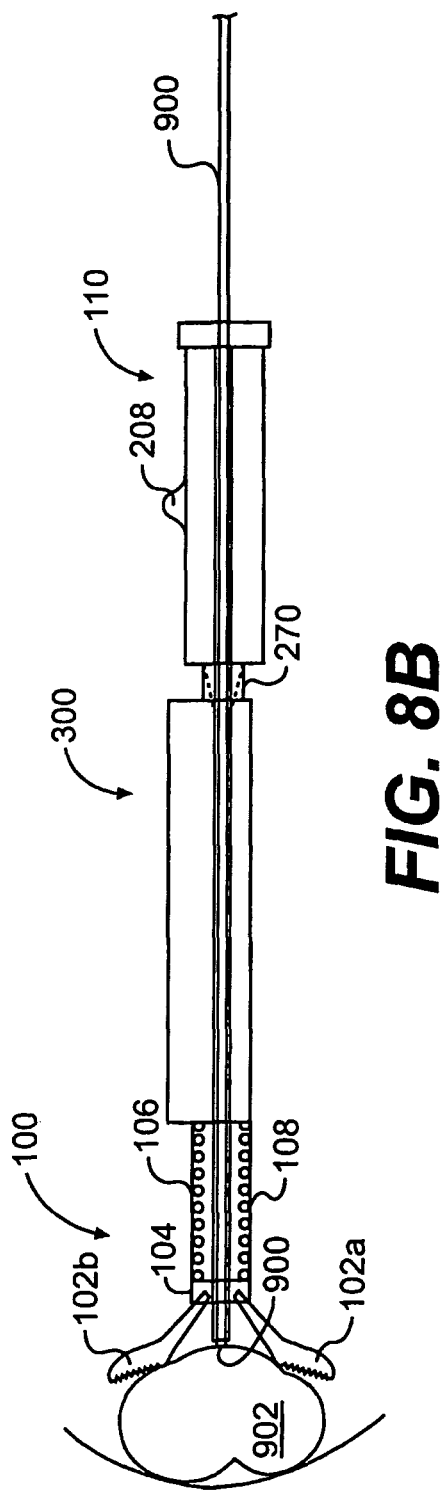

In FIG. 8a, front-loaded endoscope 300 has been inserted into the body, endoscopic device 100 is activated to open, and lithotripter 900 along with shaft 112 projects outward towards the operative site, such as stone 902. Alternatively, as shown in FIG. 8b, jaw members 102a,b are opened beyond the normal, open position. This position is obtained by operating proximal handle 110 in conjunction with endoscope 300, so that shaft 112 and ring 104 are distal relative to slide 206 and tube 106, and then moving endoscopic device 100 and endoscope 300 distally. In other words, the operator physically pushes endoscope 300 loaded with endoscopic device 100 further into the body cavity. Lithotripter 900 is then in direct contact with stone 902. Jaw members 102a,b pin stone 902 against a wall in the body, allowing continuous direct contact between lithotripter 900 and stone 902. Once stone 902 is broken down by lithotripter 900, endoscopic device 100 may or may not be used to gather the pieces.

Figure 9:
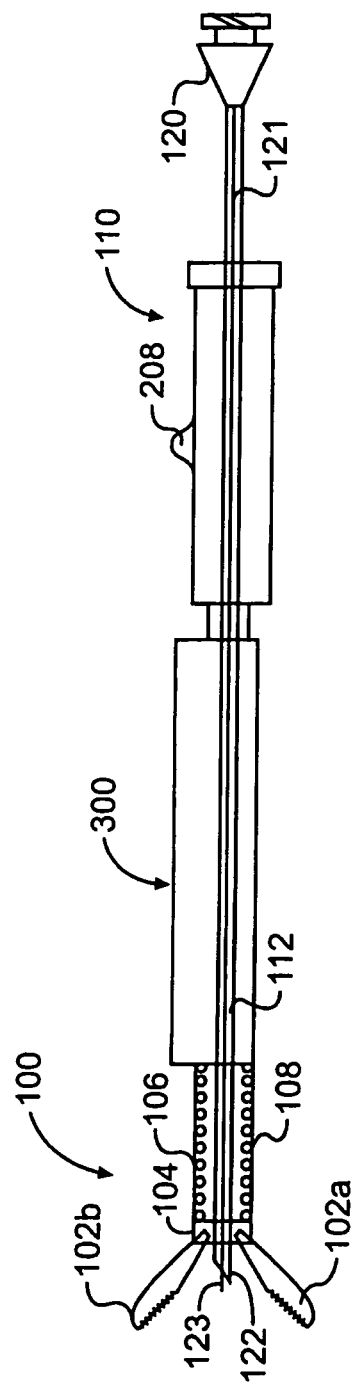
FIG. 9 is a plan view of an exemplary endoscope and endoscopic device with a needle and a hub, consistent with an embodiment of the present invention.

FIG. 9 is a plan view of an endoscopic device 100 with a needle 121 connected to hub 120, consistent with an embodiment of the present invention. In this embodiment, needle 121 enters through shaft 112 and has needle point 123 on its distal end. Alternatively, or in conjunction with needle 121, distal end of shaft 112 may be sharpened to a needle point 122, also shown in FIG. 9. Again, as described above, needle 121 or needle point 122 is inserted into the tissue by physically moving endoscope 300 loaded with endoscopic device 100 distally further into the patient. The needle has many uses, several of which are disclosed for descriptive purposes only, but are in no way limiting of the invention. The needle may provide stabilization for securely anchoring endoscopic device 100 to the desired operative site for effective sampling and accurate diagnosis. The needle also may be used as a sclerotherapy needle to swell a lesion while endoscopic device 100 biopsies the lesion. Alternatively, hub 120 may be provided with a medical luer 324 (FIG. 3b), through which an operator can administer an injection to the operative site through the needle. In addition to lithotripters and needles, other components may be inserted through shaft 112, including but not limited to, a laser probe, suction and/or irrigation means, a mechanical probe, an ultrasound probe, and a loop or snare, the operation of which are known to medical personnel and those of ordinary skill in the art.

Figure 10A:
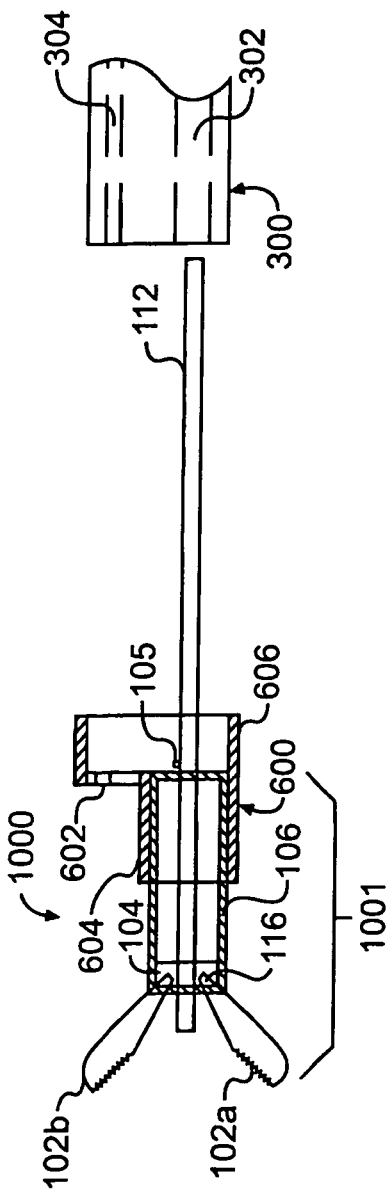
FIGS. 10a-10c are plan views of another exemplary endoscopic device without a proximal handle, consistent with an embodiment of the present invention.
Figure 10B:
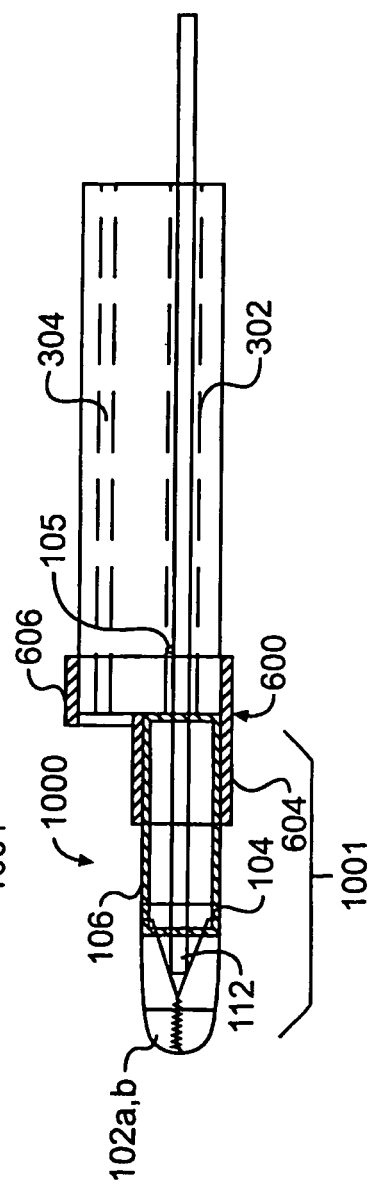
Figure 10C:
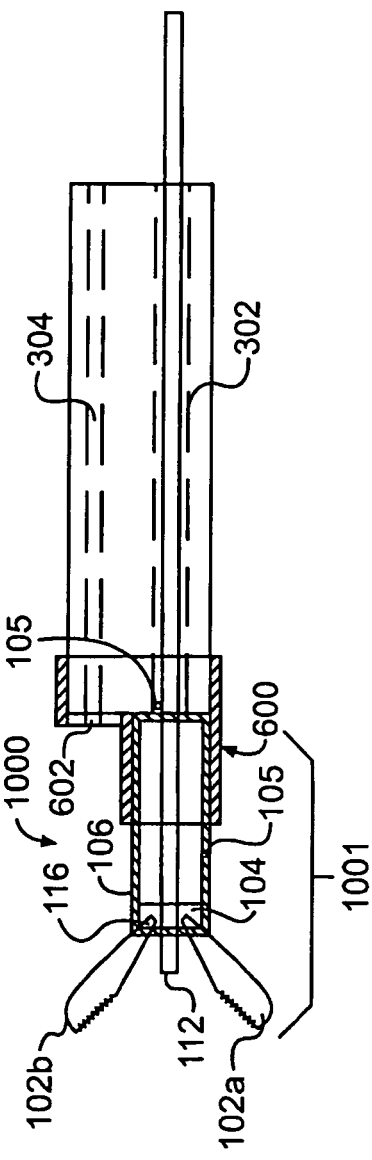

Another exemplary endoscopic device 1000 is illustrated in FIGS. 10a-10c according to an embodiment of the present invention. In many respects, endoscopic device 1000 operates similarly to the exemplary devices shown in FIGS. 1-9. Distal forceps assembly 1001, including for example jaw members 102, are activated by operation of shaft 112, and also may be used in conjunction with proximal handle 110. In this example, however, the structure of endoscopic device 1000 differs from the previously described exemplary endoscopic devices in that device 1000 includes an attachment cup 600 attached to tube 106 and does not include proximal handle 110 and spring 108 of prior embodiments, as shown in FIG. 10a. Additionally, shaft 112 is relatively stiff, and distal assembly remains closed or deactivated in tube 106, and does not automatically assume a normally open position as in previously described embodiments. For example, jaw members 102a,b are closed and partially withdrawn into tube 106, unless the operator moves shaft 112 distally to eject jaw members 102a,b.

Exemplary attachment cup 600 has a first portion 604 for attaching proximal end of tube 106 and a second portion 606 for attaching distal end 300a of endoscope 300, but any attachment cup 600 configured to secure tube 106 to endoscope 300 is sufficient. First portion 604 has a diameter that mates with that of tube 106 while second portion 606 has a diameter that mates with that of distal end of endoscope 300a. Attachment cup 600 has a hole 602 in second portion 606, or second portion 606 may be ring shaped with a hollow center, so that the operator can see through viewport 306 when attachment cup 600 is secured to endoscope 300.

Attachment cup 600 may be screwed onto, friction-fitted, coupled to, or otherwise attached to endoscope 300 to ensure a secure connection of endoscopic device 1000 with the distal end of endoscope 300a, allowing shaft 112 to push against ring 104 to eject jaw members 102a,b (as will be described below) without tube 106 separating from distal end of endoscope 300a. Although it is not shown in FIGS. 5b-5c, attachment cup 600 also may be implemented on endoscopic device 100 with proximal handle 110, shown in FIGS. 1-9, to ensure a tighter connection between tube 106 and endoscope 300 and enhance the operative performance. Similarly, spring 108 may be used in conjunction with attachment cup 600 to assist in the activation of jaw members 102, but is not required because the natural tendency of jaw members 102 to open with the movement of shaft 112 can cause jaw members 102 to open and close.

FIG. 10b is endoscopic device 1000 of FIG. 10a in a closed position and loaded in endoscope 300, while FIG. 10c is endoscopic device 1000 an open position and loaded in endoscope 300. Endoscopic device 1000 is front-loaded, meaning device 1000 is loaded by inserting its proximal end through the distal end of working channel 302 of endoscope 300. Endoscope 300 then may be inserted into the body and distal assembly 1001 activated to perform an operative procedure. A proximal handle similar to proximal handle 110 may be attached to the proximal end of shaft 112 after distal assembly 1001 is loaded, but is not shown or required.

Exemplary endoscopic device 1000 in FIGS. 10a-10c is activated to open (FIG. 10c) and reclose (FIG. 10b) by operation of shaft 112. In FIG. 1b, shaft 112 is connected to ring 104, which is in turn connected to jaw members 102a,b. If an operator holds proximal end of endoscope 300b and manually pushes (or uses proximal handle 110 to push) shaft 112 distally, ring 104 also moves distally, and jaw members 102a,b attached to ring 104 project from tube 106. Cup attachment 600 ensures that tube 106 stays fixed relative to endoscope 300 when shaft 112 is forced in a distal direction so that ring 104 and jaw members 102 can move distally relative to tube 106. Jaw members 102a,b open as they project from tube 106 for reasons previously discussed, including, for example, the properties of the "memory" material of which jaw members 102a,b may be made. As previously described, stop 105 on shaft 112 abuts the proximal end of tube 106, which prevents jaws 102, shaft 112, and ring 104 from projecting distally beyond tube 106. To reclose jaw members 102a,b, the operator pulls shaft 112 proximally while holding proximal end of endoscope 300b, and the walls of tube 106 force jaw members 102a,b to close. Otherwise, the loading, insertion, guidance, activation, operation, and withdrawal are performed as described above with respect to the exemplary endoscopic device 100 illustrated in FIG. 1a.

Figure 11A:
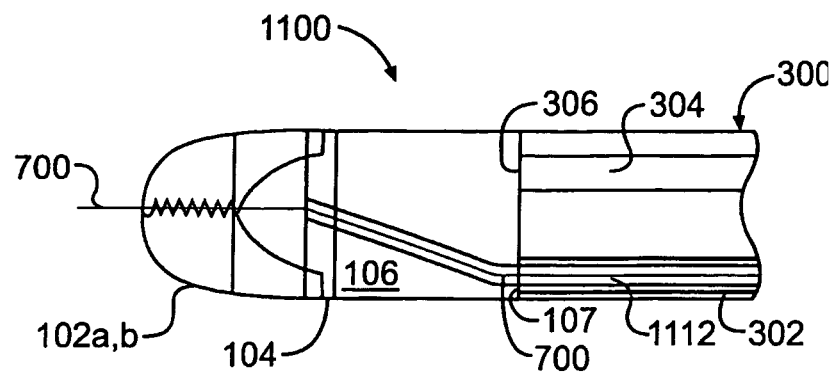
FIGS. 11a and 11b are another exemplary endoscope and endoscopic device introduced to an operative site by a guide, with the endoscopic device being in an aligned position and a rotated position with respect to the endoscope, respectively, according to an embodiment of the present invention.
Figure 11B:
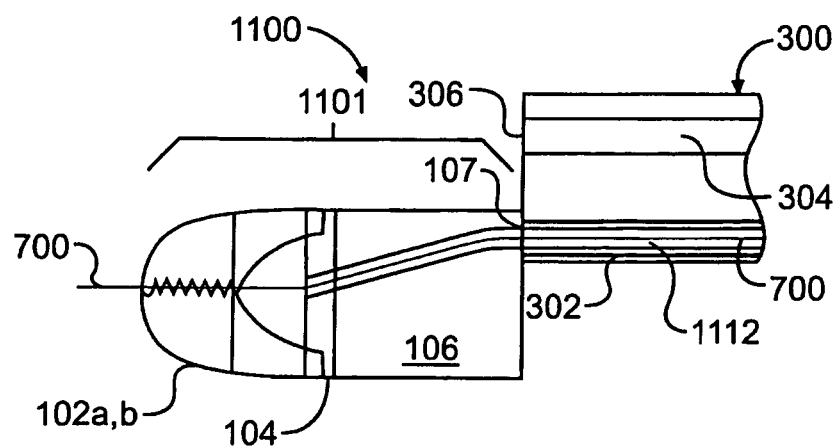

Another exemplary endoscopic device 1100 according to an embodiment of the present invention is illustrated in FIGS. 11a-11b. In this embodiment, endoscopic device 1100 is rotatable by an activation shaft 1112 to an aligned position relative to the distal end of endoscope 300 (FIG. 11a) and an unaligned position relative to the distal end of endoscope 300 (FIG. 11b). In this example, the diameter of tube 106 is approximately equal to or larger than that of distal end of endoscope 300a, or is of such size or shape, so that viewport 306 of optic channel 304 may be blocked by the distal assembly of endoscopic device 1100, as shown in FIG. 11a. In this exemplary embodiment, endoscopic device 1100 may be rotated to offset it from endoscope 300 and expose viewport 306, as shown in FIG. 11b, by rotating shaft 1112. Except for the described differences, exemplary endoscopic device 1100 is similar in structure and operation to endoscopic device 100 illustrated in and described with respect to FIGS. 1-9, although spring 108 and a proximal handle 110 are not required.

Structurally, as opposed to being straight, activation shaft 1112 of a distal assembly 1100 is bent, or angled, at its distal end, the distal end of which is attached to ring 104. At least the distal portion of shaft 1112 therefore must be made of a biocompatible material that is fairly rigid so that the angle is maintained. Hole 107 at the proximal end of tube 106 is not centered in that tube. Instead, hole 107 aligns with the distal end of channel 302 so that so that the tip of shaft 1112 couples to the center of ring 104 (and is therefore centered in tube 106). As in FIGS. 1a-1b, tube 106 is hollow, and the distal end of tube 106 is open, while the proximal end is closed except for hole 107.

Operationally, the loading of exemplary endoscopic devices 1100 and 100 differ. Endoscopic device 1100 is guided to the operative site by a guidewire or other guidance device that has been previously inserted into the body, as described for guide 700 described with respect to FIG. 6. Briefly, guide 700 is placed at a desired location by loading an endoscope into the body, inserting and placing guide 700, and removing the endoscope. Endoscopic device 1100 is then inserted in the body by inserting guide 700 into the distal end of device 1100 and guiding device 1100 it to the site. Fluoroscopy or other suitable imaging can be used in conjunction with guide 700 to confirm the correct placement of endoscopic device 1100.

Once endoscopic device 1100 is placed within the body, the proximal end of shaft 1112 is inserted into distal end 300b of working channel 302 of endoscope 300. Scope 300 is then guided to the operative site along shaft 1112 using viewport 306 until distal end 300a abuts tube 106. Because of the alignment of tube 106 and endoscope 300, viewport 306 becomes blocked upon this abutment, as shown in FIG. 11a.

An operator then rotates proximal handle 110 (or shaft 1112 if a handle is not used) of endoscopic device 1100 from the proximal end of the shaft, and due to the bent configuration of the distal end of shaft 1112 and the connection of shaft 1112 with ring 104 and jaw members 102, distal forceps assembly 1101 also rotates and no longer blocks viewport 306. Endoscopic device 1100, now in an unaligned position with respect to endoscope 300, is then operated by pushing or pulling on shaft 1112, as described for endoscopic device 1000 with respect to FIGS. 10a-10c, to perform its intended function. Endoscopic device 1100 is configured so that when shaft 1112 is retracted to the point where the bend prevents further proximal movement, jaw members 102 are fully retracted into tube 106. When the procedure is complete, endoscopic device 1000 may be re-rotated into alignment with endoscope 300 and removed from the body.

Another exemplary endoscopic device 1200 is illustrated in FIG. 12a, according to an embodiment of the present invention. Endoscopic device 1200 may be structurally and operationally similar to the exemplary devices shown in FIGS. 1, 10, and 11, except that endoscopic device 1200 has an extension tube 1202 and is back-loaded into an exemplary endoscope 350 having a large working channel 355.

Extension tube 1202 is an elongate, flexible member having a diameter of approximately the same size as tube 106 and proximal handle 110. The distal end of extension tube 1202 abuts or is connected to the proximal end of tube 106, while the proximal end of extension tube 1202 abuts or is connected to the distal end of proximal handle 110. The length of extension tube 1202 is dependent upon the distance to the operative site, and is long enough to extend from proximal handle 110 located outside the body to distal assembly 101 at the operative site. Extension tube 1202 may be made of any flexible or semi-flexible biocompatible material, such as rubber or plastic, that is rigid enough to abut tube 104 and proximal handle 110 without collapsing or folding upon abutting other components.

The assembly of endoscopic device 1200 and its insertion into a body differ from that of the exemplary embodiments illustrated and described with respect to FIGS. 1-11. Proximal end of shaft 112 is inserted through the distal end of extension tube 1202 until the proximal end of tube 106 abuts extension tube 1202, and cap 210 of proximal handle 110 is attached to the proximal end of shaft 112 (as previously described), where proximal handle 110 abuts extension tube 1202. Although FIG. 12a depicts an endoscopic device without an attachment cup, an attachment cup, such as that shown in FIG. 10, may also be used.

Endoscope 350, having a working channel 355 with a larger diameter than the diameter of distal assembly 101 or extension tube 1202, is then loaded into a body to reach an operative site. As an example only, working channel 355 may be 7 Fr. and distal assembly 101 and extension tube 1202 may be 5 Fr. Endoscopic device 1200 is then inserted into the proximal end of working channel 355 until distal assembly 101 projects from the distal end of endoscope 350 (not shown).

Once loaded, endoscopic device 1200 is operated in essentially the same manner as those devices in FIGS. 1-11, except that instead of endoscope 300 abutting or attaching to distal assembly 101 and operating in conjunction with distal assembly 101, extension tube 1202 abuts or is attached to and operates in conjunction with distal assembly 101.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of performing an operative procedure with an endoscopic device having a distal assembly including a tube, comprising:
    loading the endoscopic device into a channel of an endoscope, wherein the endoscope includes a plurality of channels, each of the plurality of channels extending from a proximal end of the endoscope to a distal end of the endoscope;
    inserting the endoscope and the endoscopic device into a body while the distal assembly is exterior the channel and is in a closed configuration with a profile larger than a diameter of the channel of the endoscope;
    positioning the distal assembly proximate an operative site; and
    activating the distal assembly to perform the operative procedure by opening and closing the distal assembly, wherein, when the distal assembly is in an open configuration, a distal end of an elongate member extends distally of a distal end of the tube, the elongate member including an elongate lumen within the elongate member and extending from a proximal end to the distal end of the elongate member, wherein the elongate member moves axially relative to the tube.

2. The method of claim 1, further comprising removing the endoscope and the endoscopic device from the body, while the distal assembly is exterior to the channel.

3. The method of claim 1, wherein activating the distal assembly includes moving the elongate member connected to the distal assembly relative to the endoscope, the elongate member passing through the channel and having a length greater than a length of the channel.

4. The method of claim 1, wherein activating the distal assembly includes activating a proximal handle of the endoscopic device.

5. The method of claim 4, wherein activating the proximal handle causes the elongate member to move proximally relative to the endoscope.

6. The method of claim 5, wherein the distal end of the endoscope contacts the tube of the distal assembly, wherein the elongate member moves proximally relative to the tube.

7. The method of claim 6, wherein the distal assembly includes jaw members, and movement of the elongate member proximally relative to the tube causes the jaw members to close.

8. The method of claim 4, further comprising removing the proximal handle from the elongate member of the endoscopic device before loading the endoscopic device into the channel.

9. The method of claim 4, further comprising attaching the proximal handle to the elongate member of the endoscopic device after the endoscopic device is loaded in the channel.

10. The method of claim 1, wherein the operative procedure includes obtaining at least one tissue sample.

11. The method of claim 10, further comprising storing the at least one tissue sample in the distal assembly.

12. The method of claim 1, wherein the distal assembly includes a forceps device.

13. The method of claim 12, wherein the forceps device includes a jaw assembly that is attached to a proximal handle by the elongate member, the elongate member passing through the channel.

14. The method of claim 13, further comprising opening and closing the jaw assembly by activating the proximal handle.

15. The method of claim 14, wherein activating the proximal handle causes the elongate member to move proximally relative to the endoscope.

16. The method of claim 15, wherein the distal end of the endoscope contacts the tube of the distal assembly, wherein the elongate member moves proximally relative to the tube.

17. The method of claim 13, wherein the jaw assembly includes jaw members, and movement of the elongate member proximally relative to the tube causes the jaw members to close.

18. The method of claim 1, further comprising guiding the endoscope and the endoscopic device to the operative site with a guide.

19. The method of claim 1, further comprising loading a medical device through the elongate member of the endoscopic device, wherein the elongate member has a length greater than a length of the channel of the endoscope.

20. The method of claim 1, wherein loading the endoscope further comprises inserting the proximal end of the elongate member into a distal end of the channel of the endoscope, wherein the distal end of the elongate member is connected to the distal assembly, and wherein a length of the elongate member is greater than a length of the channel.

21. The method of claim 1, wherein activating the distal assembly includes rotating an activation shaft.

22. A method of performing an operative procedure with an endoscopic device having a distal assembly including a tube, comprising:
   loading the endoscopic device into a channel of an endoscope, wherein the endoscope includes a plurality of channels, each of the plurality of channels extending from a proximal end of the endoscope to a distal end of the endoscope;
   inserting the endoscope and the endoscopic device into a body while the distal assembly is exterior the channel and is in a closed configuration with a profile larger than a diameter of the channel of the endoscope;
   positioning the distal assembly proximate an operative site; and
   activating the distal assembly to perform the operative procedure by opening and closing the distal assembly by actuating an elongate member, the elongate member including an elongate lumen within the elongate member and extending from a proximal end to a distal end of the elongate member,
   wherein the elongate member moves axially relative to the tube.

23. A method of performing an operative procedure with an endoscopic device having a distal assembly including a tube, comprising:
   loading the endoscopic device into a channel of an endoscope, wherein the endoscope includes a plurality of channels, each of the plurality of channels extending from a proximal end of the endoscope to a distal end of the endoscope;
   inserting the endoscope and the endoscopic device into a body while the distal assembly is exterior the channel and is in a closed configuration with a profile larger than a diameter of the channel of the endoscope;
   positioning the distal assembly proximate an operative site; and
   activating the distal assembly to perform the operative procedure by opening and closing the distal assembly by actuating an elongate member, the elongate member including an elongate lumen within the elongate member and extending from a proximal end to a distal end of the elongate member, wherein the elongate member moves axially relative to the tube, wherein performing the operative procedure includes:
   obtaining and storing a first tissue sample within the distal assembly; and
   obtaining and storing a second tissue sample within the distal assembly.

24. A method of performing an operative procedure with an endoscopic device having a distal assembly including a tube, comprising:
   loading the endoscopic device into a channel of an endoscope, wherein the endoscope includes a plurality of channels, each of the plurality of channels extending from a proximal end of the endoscope to a distal end of the endoscope;
   inserting the endoscope and the endoscopic device into a body while the distal assembly is exterior the channel and is in a closed configuration with a profile larger than a diameter of the channel of the endoscope;
   positioning the distal assembly proximate an operative site; and
   activating the distal assembly to perform the operative procedure by opening and closing the distal assembly by actuating an elongate member, the elongate member including an elongate lumen within the elongate member and extending from a proximal end to a distal end of the elongate member, wherein the elongate member moves axially relative to the tube, wherein performing the operative procedure includes obtaining and storing a tissue sample within the distal assembly, wherein the distal assembly includes a plurality of jaws, each of the plurality of jaws including a proximal portion configured to retract longitudinally into the tube when the distal assembly is closed.

* * * * *

UNITED STATES PATENT AND TRADEMARK OFFICE
CERTIFICATE OF CORRECTION

| | | |
|---|---|---|
| PATENT NO. | : 8,409,243 B2 | Page 1 of 1 |
| APPLICATION NO. | : 11/640251 | |
| DATED | : April 2, 2013 | |
| INVENTOR(S) | : Chu | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 893 days.

Signed and Sealed this
Twenty-third Day of September, 2014

Michelle K. Lee
*Deputy Director of the United States Patent and Trademark Office*